United States Patent [19]

Campbell et al.

[11] Patent Number: 4,785,124

[45] Date of Patent: * Nov. 15, 1988

[54] PROCESS FOR PREPARING HIGHER ORDER CUPRATE COMPLEXES

[75] Inventors: Arthur L. Campbell, Glenview; James R. Behling, Lindenhurst; Sau-hoi N. John, Chicago; Kevin A. Babiak, Evanston, all of Ill.

[73] Assignee: G. D. Searle & Co., Chicago, Ill.

[*] Notice: The portion of the term of this patent subsequent to Oct. 12, 2005 has been disclaimed.

[21] Appl. No.: 59,294

[22] Filed: Jun. 8, 1987

[51] Int. Cl.$^4$ .............................. C07F 1/08; C07F 7/22
[52] U.S. Cl. ........................................ 556/28; 556/87; 556/112
[58] Field of Search ..................... 556/112, 87, 28

[56] References Cited

U.S. PATENT DOCUMENTS

| Re. 30,287 | 5/1980 | Marx et al. | 556/112 X |
|---|---|---|---|
| 3,965,143 | 6/1976 | Collins et al. | 556/112 X |
| 4,271,314 | 6/1981 | Collins | 560/121 |
| 4,322,543 | 3/1982 | Collins | 556/436 |
| 4,499,296 | 2/1985 | Collins | 560/118 |
| 4,529,812 | 7/1985 | Collins | 560/121 |
| 4,578,505 | 3/1986 | Collins | 560/118 |

OTHER PUBLICATIONS

Lipshutz "Applications of Higher Order Mixes Organocuprates to Organic Synthesis:," Synthesis, 4, p. 325 (1987).
Bindra and Bindra, "Prostaglandin Synthesis", Academic Press, Inc. N.Y. Chapter 7, pp. 99–108.
Collins, J. Med. Chem., 29, 437 (1986).
Corey, et al., J.A.C.S., 94, 7210–11 (1972).

Primary Examiner—Paul F. Shaver
Attorney, Agent, or Firm—Mary Jo Kanady; Paul D. Matukaitis

[57] ABSTRACT

This invention encompasses a process for preparing higher order cuprate complexes which contain a carbanion for the formation of carbon to carbon bonds in reactions such as epoxide addition. The complex is formed by reacting a first cuprate complex with a stannane such that the carbanion to be used to form carbon to carbon bonds is transferred from the stannane to the first cuprate complex to form a different higher order cuprate complex. This process permits the in situ preparation of a higher order cuprate complex having the carbanion desired to be used in a synthetic reaction. Higher order cuprate complexes derived from the reaction of a cuprate complex with 1,2-bis-tri-n-butylstannyl ethylene are particularly useful for the addition to epoxides to form vinyl tin intermediates useful for preparing omega side chains of prostaglandins.

2 Claims, No Drawings

PROCESS FOR PREPARING HIGHER ORDER CUPRATE COMPLEXES

BACKGROUND OF THE INVENTION

I. Field of the Invention

This invention is in the field of preparing higher order cuprate complexes from vinyl stannane compounds as reactive intermediates in organic synthesis. Higher order cuprate complexes derived from the reaction of a cuprate complex with 1,2-bis-tri-n-butylstannyl ethylene are particularly useful for the addition to epoxides to form vinyl tin intermediates that are useful for preparing omega side chains of prostaglandins, particularly 16-hydroxy prostaglandin side chains.

II. Prior Art

The state of the art of higher order cuprate complexes is summarized in *Synthesis*, #4, p. 325, (1987) where higher order cuprate complexes of the formulae $R_tRCu(CN)Li_2$, $R_tCu(2\text{-thienyl})CNLi_2$, and $R_tRCu(SCN)Li_2$ and their use are disclosed. $R_t$ represents the group transferred to an organic compound to form a carbon to carbon bond in a subsequent reaction with the complex.

U.S. Pat. No. 4,499,296 describes the preparation of a large number of prostaglandins prepared by the sequence of reactions set out in the following steps:

(i) a stannane compound of the formula

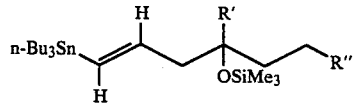

is reacted with alkyl lithium in one reaction vessel;

(ii) an organo copper compound is formed in a separate vessel;

(iii) the reagents formed in (i) and (ii) are mixed together and added to a cyclopentenone:

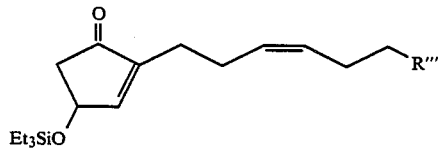

to provide prostaglandins of formula I

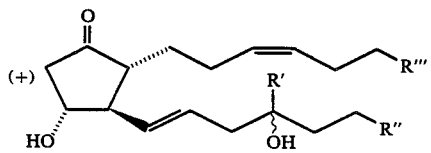

wherein,

R'''' is —CO₂R'''';

R'''' is hydrogen or lower alkyl containing 1 to 6 carbon atoms;

R' is lower alkyl containing 1 to 6 carbon atoms, vinyl or ethynyl;

R'' is alkyl or cycloalkyl containing 3 to 5 carbon atoms; and the wave line represents R,S stereochemistry.

JACS 94 7210 (1972) describes lithium copper vinyl complexes. *Prostaglandin Synthesis,* Academic Press, 1977, Chapt. 7 describes prostaglandin synthesis generally. U.S. Pat. Nos. 4,449,926; 4,322,543; 4,578,5050; and 4,271,314 describe organotin intermediates in the preparation of prostaglandins.

BRIEF DESCRIPTION OF THE INVENTION

This invention encompasses a process for preparing a higher order cuprate complex comprising bringing into reactive contact a first cuprate complex of the formula:

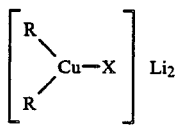

or

wherein:

(a) X is —CN, —SCN, —O—SO₂CF₃ or —S-phenyl;

(b) each R is independently lower alkyl, alkenyl, phenyl, naphthyl, phenanthryl, or thienyl, provided that (i) each of the aforementioned radicals may be substituted with non-interfering substituents and (ii) only one R in the first cuprate complex may be alkenyl, phenyl, naphthyl, phenanthryl, or thienyl; and (c) each R¹ is independently lower alkyl;

with a stannane compound of the formula:

wherein each R² represents independently lower alkyl and R_t represents a vinyl carbanion for carbon to carbon bond formation reactions of the formula:

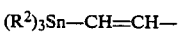

whereby R_t replaces at least one R on Cu. The resulting cuprate complexes are advantageously added to epoxides to form intermediates in the preparation of the omega side chain of prostaglandins. More specifically, these vinyl tin intermediates are especially useful for the synthesis of omega side chains for 16-hydroxy prostaglandins.

In accordance with the present invention it is not necessary to first react the organo stannane compound with alkyl lithium in one reaction vessel, preparing an alkyl copper in a second reaction vessel and then combine the two reagents to form the cuprate complex suitable for reactions such as 1,4-conjugate addition to cyclopentenones. In this invention, the higher order cuprate complex is prepared in situ by transferring directly from a stannane compound to a cuprate complex the ligand (R_t) to be used in a synthetic organic reaction to form a new carbon to carbon bond. This in situ preparation is exemplified by the following reaction (Scheme 1):

Scheme I

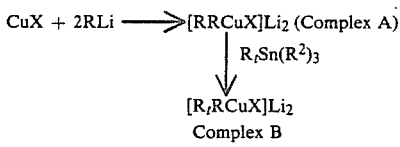

Complex B of Scheme 1 is useful in a wide variety of organic synthetic reactions to add $R_t$ to receptive compounds such as epoxides.

DETAILED DESCRIPTION OF THE INVENTION

This invention encompasses a higher order reactive cuprate complex prepared by the process of bringing into reactive contact a first cuprate complex of the formula:

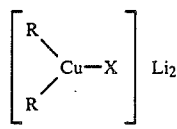

or

[R—Cu—(CN)$_2$]LiN(R$^1$)$_4$ wherein:
(a) X is —CN, —SCN, —O—SO$_2$CF$_3$ or —S-phenyl
(b) each R is independently lower alkyl, alkenyl, phenyl, naphthyl, phenanthryl, or thienyl, provided that (i) each of aforementioned radicals may be substituted with non-interfering substituents and (ii) only one R in the first cuprate complex may be alkenyl, phenyl, naphthyl, phenanthryl, or thienyl; and
(c) each R$^1$ is independently lower alkyl;
with a stannane compound of the formula:

wherein each R$^2$ represents independently lower alkyl and R$_t$ represents a vinyl carbanion for carbon to carbon bond formation reactions of the formula:

whereby R$_t$ replaces at least an R on Cu.

By lower alkyl is meant straight or branched chain alkyl having 1 to 6 carbon atoms or cycloalkyl having 3 to 6 carbon atoms.

By non-interfering substituent is meant substituents such as lower alkyl, lower alkoxy, halo, lower alkanoyl, phenyl, cyano, phenoxy and the like which do not react with the cuprate complex and sterically or electronically hinder the reaction.

The higher order cuprate complex of this invention is generally formed in either an alkyl ether solvent where the alkyl groups have 1 to 6 carbon atoms, or in a cycloalkyl ether solvent having 4 to 8 carbon atoms such as tetrahydrofuran or tetrahydropyranes, or in alkane solvents having 5 to 8 carbons or mixtures thereof. These reactions are typically conducted at a temperature of about —40° C. to about 30° C.

Referring to reaction Scheme 1, typically about two moles of alkyl lithium in a hydrocarbon solvent is reacted with about one mole of copper cyanide or thiocyanide in tetrahydrofuran, for example, at about 0° C., then about one mole of R$_t$Sn(R$^2$)$_3$ in tetrahydrofuran is added to form higher order cuprate complex (Complex B). Alternatively, about one mole of alkyl lithium is reacted with about one mole of a lower order cuprate (RCuXLi) (commercially available where R is thienyl) in tetrahydrofuran at about 0° C., then about one mole of R$_t$Sn(R$^2$)$_3$ in tetrahydrofuran is added to form a higher order cuprate complex (Complex B). Complex B is then reacted with, for example, an epoxide at about —15° C. and the reaction mixture is allowed to warm to 0° C. The epoxide addition product is then isolated by art recognized techniques.

In a preferred embodiment, a cuprate complex of the formula

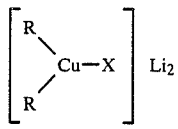

wherein one R is lower alkyl and one R is thienyl, and wherein X is —CN, is reacted with a vinyl tin compound of the formula

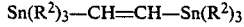

wherein Sn(R$^2$)$_3$—CH=CH—Sn(R$^2$)$_3$ is used to derive the omega chain of a natural or synthetic prostaglandin. These vinyl tin compounds are made by art recognized techniques. For example, one preferred vinyl tin compound is 1,2-bis-tri-n-butylstannyl ethylene which is prepared according to the procedure of A. N. Mesmeyanov and A. E. Boisov, *Dokl. Akad. Nauk SSSR*, 174, 96 (1967).

DESCRIPTION OF PREFERRED EMBODIMENTS

The following scheme illustrates a preferred embodiment:

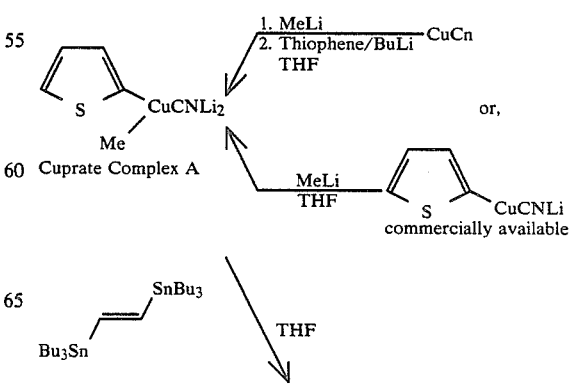

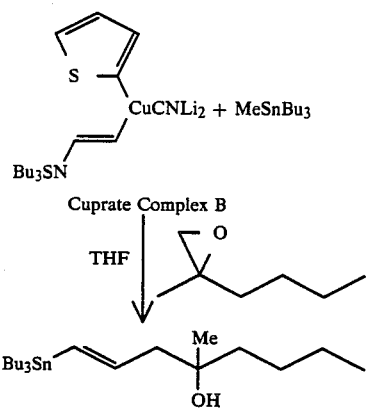

The reaction and all transfers are done under an argon atmosphere and the tetrahydrofuran (THF) is non-stabilized.

EXAMPLE 1

In Situ Formation of 2-Thienyl β-tributylstannylethenyl Copper Cyanide to Prepare a Vinyl Tin Intermediate Useful for the Preparation of the Omega Side Chain of a Prostaglandin To copper cyanide (756 mg, 8.44 mol) flame dried under vacuum after addition to a 100 ml reactor and cooled under Argon is added tetrahydrofuran (6 ml). The resulting heterogenous mixture is cooled to 0° C. and methyl lithium (6.8 ml, 1.49M in diethylether, 10.1 mmol) is added slowly. During the addition, the temperature of the reaction mixture warms to 18°-22° C. and the mixture becomes homogenous. The resulting homogenous solution is cooled to 0° C. and a tetrahydrofuran (10 ml) solution of lithiothiophene that had been previously prepared by the addition of butyllithium (2.27M in hexane, 3.72 ml, 8.44 mmol) to a tetrahydrofuran (10 ml) solution of thiophene (0.677 ml, 8.45 mmol) at −60° C. is added via cannula. Alternatively, methyl lithium (6.8 mL, 1.49M in diethyl ether, 10.1 mmol) is added to a cooled solution (0° C.) of commercially available lithium 2-thienyl cyano cuprate (21.0 mL, 0.48M in tetrahydrofuran) to prepare Complex A. To the resulting homogenous reaction mixture is added a tetrahydrofuran (2 ml) solution of 1,2-bis-tri-n-butyl-stannyl ethylene (5.88 g, 9.7 mmol, degassed under high vacuum) via cannula. The mixture is warmed to ambient temperature until cuprate formation (Complex B) is complete as determined by vapor phase chromatography (VPC) analysis of a quenched aliquot, 1 to 3 hours normally. The mixture is cooled to −15° C. and 2-methyl-1,2-epoxyhexane (775 mg, 6.8 mmol) in tetrahydrofuran (3 ml) is added via syringe. The reaction mixture is allowed to come to 0° C. for 18 hours after which it is quenched by addition to a solution of saturated ammonium chloride (45 ml) and concentrated ammonium hydroxide (5 ml). After stirring for 30 minutes, the aqueous mixture is extracted with three portions of diethyl ether (50 ml). The extracts are combined, dried over sodium sulfate and concentrated under vacuum to provide an oil containing the vinyl tin intermediate useful for preparing omega side chains of prostaglandins which can be isolated from the oil by liquid chromatography in 70 to 80% yield. 1,2-Bis-tri-n-butylstannyl ethylene is prepared according to the procedure of A. N. Mesmeyanov and A. E. Boisov, *Dokl. Akad. Nauk SSSR*, 174, 96 (1967). 1-methyl-1,2-epoxyhexane is prepared according to the procedure of V. Franzen and H. E. Driessen, *Chem. Ber.*, 96, 1881 (1963).

EXAMPLE 2

Preparation of the Chiral Omega Side Chain of Prostaglandins Via The In Situ Formation of 2-Thienyl β-Tributylstannylethenyl Copper Cyanide and a Chiral Epoxide The required chiral 2-methyl-1,2-epoxyhexane was obtained from (2R) or (2S)-2-hydroxy-2-methylhexan-1-ol, prepared as described by J. S. Yadav, P. S. Reddy and R. S. Jolly, *Indian J. Chem.*, 25B, 294 (1986) as follows. To ice cooled methylene chloride (20 mL) was added consecutively, (2S)-2-methylhexan-1-ol (5.04 g, 38.1 mmol), pyridine (5.53, 70.0 mmol) and p-toluenesulfonyl chloride (10.83, 57 mmol). The resulting homogeneous mixture was stirred at 25° C. overnight and then poured onto ice. After stirring for an additional 30 minutes the mixture was extracted with ethyl acetate (2×50 mL). The organics were combined, washed with cold 1.0N HCl (50 mL), sat'd NaHCO₃ (50 mL), sat'd NaCl (50 mL), dried (MgSO₄), filtered and concentrated to provide the desired primary tosylate (10.91 g). To a cooled (0° C.) solution of the crude tosylate (10.70 g, 37.4 mmol) in methylene chloride/water (1/1, 50 mL) containing tetrabutyl ammonium sulfate (201 mg, 0.60 mmol) was added dropwise 50% NaOH (3.60 mL, 45 mmol). After stirring at 25° C. for 1.5 h the mixture was diluted with methylene chloride and extracted with water (3×25 mL), sat'd NaCl (25 mL), dried (MgSO₄), filtered and frictionally distilled to provide (2S)-2-methyl-1,2-epoxyhexane (3.50 g, bp 129°-131.5° C.) in 82% yield. This chiral epoxide was converted to the desired 16(S)-vinyl tin intermediate according to the methods described in Example 1.

What is claimed is:

1. A process for preparing a higher order cuprate complex comprising bringing into reactive contact a first cuprate complex of the formula:

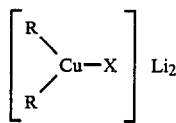

or

wherein:
(a) X is —CN, —SCN, —OSO₂—CF₃, or —S-phenyl;
(b) each R is independently lower alkyl, alkenyl, phenyl, naphthyl, phenanthryl, or thienyl, provided that (i) each of the aforementioned radicals may be substituted with non-interfering substituents and (ii) only one R in the first cuprate complex may be alkenyl, phenyl, naphthyl, phenanthryl, or thienyl; and
(c) each R¹ is independently lower alkyl;
with a stannane compound of the formula:

wherein each $R^2$ represents independently lower alkyl and $R_t$ represents a carbanion for carbon to carbon bond formation reactions of the formula:

$$(R^2)_3Sn-CH=CH-$$

whereby $R_t$ replaces at least one R on Cu.

2. A process for preparing a higher order cuprate complex comprising bringing into reactive contact a first cuprate complex of the formula:

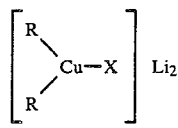

with a stannane compound of the formula:

$$R_t(SnR^2)_3$$

wherein R are each independently lower alkyl or one R is lower alkyl and the other is thienyl; X represents —CN or —SCN; each $R^2$ represents independently lower alkyl; and $R_t$ represents a carbanion for carbon to carbon bond formation wherein $R_t$ has the formula:

$$(R^2)_3Sn-CH=CH-$$

and $R_t$ displaces one R on the cuprate complex.

* * * * *

UNITED STATES PATENT AND TRADEMARK OFFICE
CERTIFICATE OF CORRECTION

PATENT NO.   : 4,785,124

DATED        : November 15, 1988

INVENTOR(S)  : Campbell, et al.

It is certified that error appears in the above-identified patent and that said Letters Patent is hereby corrected as shown below:

On the front page of the patent, in the section that lists the inventors, reading "Sau-hoi N. John" should read -- John Sau-hoi Ng --.

Column 2, line 1, reading "U.S. Pat. Nos. 4,449,926; 4,322,543; 4,578,5050" should read -- U.S. Pat. Nos. 4,449,296; 4,322,543; 4,578,505 --.

Column 3, line 64, reading "4 to 8 carbon atoms" should read -- 4 to 6 carbon atoms --.

Column 4, to the right of the second structure, line 55, reading "CuCn" should read -- CuCN --.

Column 6, line 16, reading "(2S)-2-methylhexan-1-ol" should read -- (2S)-2-hydroxy-2-methylhexan-1-ol --.

Signed and Sealed this

Seventeenth Day of April, 1990

Attest:

HARRY F. MANBECK, JR.

*Attesting Officer*                  *Commissioner of Patents and Trademarks*